United States Patent [19]
Groover

[11] Patent Number: 5,184,083
[45] Date of Patent: Feb. 2, 1993

[54] APPARATUS AND METHOD FOR THE LOCATION OF LEAKS BY ARRAYED POTENTIALS AND DERIVED VECTORS

[76] Inventor: Thomas A. Groover, 1117 W. Drew, Houston, Tex. 77006

[21] Appl. No.: 676,282

[22] Filed: Mar. 28, 1991

[51] Int. Cl.⁵ .................. G01N 27/00; G01R 31/00; G01M 3/16
[52] U.S. Cl. .................................. 324/559; 324/357; 340/605
[58] Field of Search .............................. 324/557–559, 324/357, 365; 73/49.2; 340/605

[56] References Cited

U.S. PATENT DOCUMENTS

| | | | |
|---|---|---|---|
| 2,211,124 | 8/1940 | Jakosky | 324/357 |
| 3,319,158 | 5/1967 | McDoulett et al. | 324/357 |
| 4,543,525 | 9/1985 | Boryta et al. | 324/559 |
| 4,719,407 | 1/1988 | Converse et al. | 324/559 |
| 4,720,669 | 1/1988 | Owen | 324/546 |
| 4,725,785 | 2/1988 | Converse et al. | 324/559 |
| 4,740,757 | 4/1988 | Converse et al. | 324/559 |
| 4,751,467 | 6/1988 | Cooper | 324/557 |
| 4,751,841 | 6/1988 | Biard et al. | 73/49.2 |
| 4,755,757 | 7/1988 | Cooper | 324/557 |
| 4,835,474 | 5/1989 | Parra et al. | 324/363 |
| 4,839,601 | 6/1989 | Cotterell et al. | 324/559 |
| 4,905,210 | 2/1990 | Owen | 367/128 |

*Primary Examiner*—Gerard R. Strecker
*Attorney, Agent, or Firm*—Harrison & Egbert

[57] ABSTRACT

A system of leak detection in an impoundment including a first impoundment layer containing a brine solution, a second impoundment layer positioned beneath the first impoundment layer and having a brine-filled space therebetween, a first electrode positioned in the brine-filled space, an injection electrode positioned in the brine solution on the first impoundment layer, a plurality of sensor elements extending outwardly from the injection electrode for measuring electrical potentials at points distal the injection electrode, and a source of power electrically connected to the first electrode and to the injection electrode for passing a current between the electrodes. A probe assembly is connected to the injection electrode for supporting the injection electrode above the first impoundment layer. The sensor elements are arranged generally coplanar to the injection electrode. Each of the sensor elements are separated by an equal distance from an adjacent sensor element. A processor is interconnected to the sensor elements for determining a vector of current flow from the injection electrode toward a leak in the impoundment layer.

15 Claims, 6 Drawing Sheets

FIG. 5A
FIG. 5B
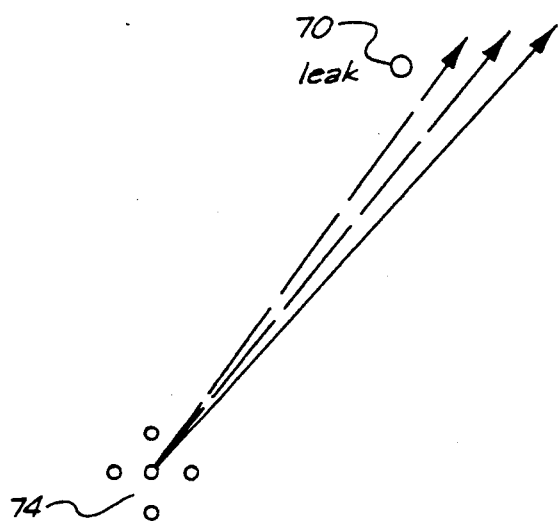
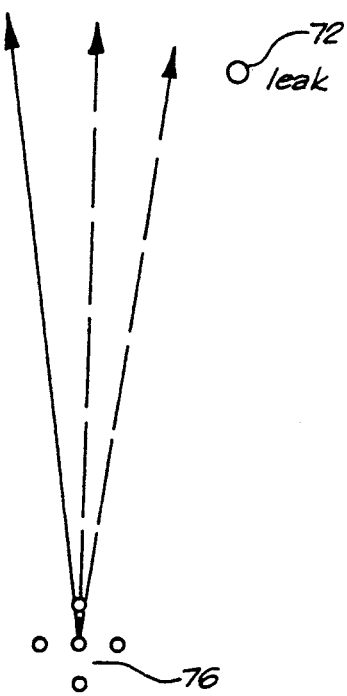

APPARATUS AND METHOD FOR THE LOCATION OF LEAKS BY ARRAYED POTENTIALS AND DERIVED VECTORS

TECHNICAL FIELD

The present invention relates to a method and apparatus for locating leaks in geomembrane liners used to contain liquids in surface impoundment facilities. More particularly, the present invention relates to the use of non-intrusive electrical measurement techniques for the purpose of obtaining precise location of leaks in geomembrane liners.

BACKGROUND ART

Impoundments are used for the storage and disposal of chemicals and wastes. The use of impoundments has increased dramatically over the recent past considering the present waste disposal problems. The possibilities presented by biological treatment of hazardous waste further contribute to the need for the creation and use of impoundments. Liquid impoundments are made by scooping out a pond or lake, typically using earth-moving equipment, and a geomembrane is spread across the pond. These geomembrane liners (often called flexible liners) are large sheets of plastic or rubber material used as a barrier so as to contain the liquids within the impoundment. Facilities where these liners are commonly used include hazardous waste landfills and liquid impoundments, water reservoirs, and other surface impoundments.

In certain types of facilities, such as hazardous liquid surface impoundments, the geomembrane liner is often comprised of two separate layers of liner material to provide an additional margin of containment. The two-layer geomembrane liner consists of a lower plastic sheet typically made of high-density polyethylene or other polymeric material, a water-permeable intermediate material made of loosely woven or fusion-bonded plastic stringers (or, in some cases, a sand layer of several inches thickness), and an upper plastic sheet similar to the lower sheet. The grade of the bottom of the impoundment is constructed with an incline to accommodate a sump drain to collect any leakage from the impoundment through the upper liner and into the interliner zone.

Previous methods for monitoring the performance of liners after installation and use have typically been based on ground water sampling using a plurality of monitoring wells at spaced intervals along the perimeter of the impoundment. The ground water sampling method, however, provides only an indirect and delayed indication of leakage and, therefore, is not adequate for monitoring liner performance since ground water contamination may take years to occur. Furthermore, by the time a leak has been determined by this method, substantial ground water contamination may have already occurred.

Another source of inadequacy in the ground water sampling method stems from the need to have the monitoring well in the particular aquifer which is transporting the contaminants. An adequate ground water monitoring program, therefore, requires a large number of monitoring wells along the perimeter of the impoundment with a sufficient number of wells sampling water from different levels within the various aquifers beneath the impoundment. Even the most elaborate ground water monitoring system, however, cannot provide monitoring as accurately and timely as necessary.

One non-intrusive method for detecting and locating leaks in geomembrane liner systems is described in U.S. Pat. No. 4,725,785, issued on Feb. 16, 1988, to Converse et al. This method uses an electrical measurement technique which takes advantage of the high electrical insulating properties of the liner with respect to the liquid contained above the liner and the soil underneath the liner. In general, geomembrane liners made from an impervious plastic material or rubber have a very high electrical resistance. A liner installed in a landfill or liquid impoundment, therefore, effectively acts as an electrical insulator between the materials contained within the facility and the surrounding environment. If the integrity of the liner is lost due to a puncture or separation, however, conductive liquid may then flow through the leak, thus establishing an electrical shunt through the liner between the contained liquid and the conductive earth in surrounding contact with the liner. The shunt is a low resistance path for current flow which forms an electrically detectable region corresponding to a leak which may be detected and located.

U.S. Pat. No. 4,755,757, issued on Jul. 5, 1988, to J. W. Cooper describes a system and method for measuring the leakage flow rate from an impounded liquid through a tear or hole in the geomembrane liner. This system utilizes a narrowed passage connected with an inverted funnel to confine the flow, and further includes forming a transverse magnetic field thereacross, a sensor mutually perpendicular to the passage and the magnetic field and a volt meter connected to the sensor for measuring the voltage. The voltage is dependent on the rate of flow of the leaked liquid across the passage.

U.S. Pat. No. 4,751,841, issued on Jun. 21, 1988, to Biard et al. describes a detector for use in determining the rate of loss of liquid from an impoundment. This device includes first and second open ended columns for receiving the impounded liquid therein. The first column is isolated while the second column is communicated near the bottom thereof with a passage into the impoundment so that its height will fall with the height of liquid in the impoundment. A measuring means is interposed between the two columns to measure differences in height. The two columns are equipped with baffles to suppress column height agitation.

U.S. Pat. No. 4,751,467, issued on Jun. 14, 1988, to J. W. Cooper describes another method and apparatus for determining the rate of flow of a leak through a geomembrane. A surrounding lower skirt having a peripheral weight thereabout is placed on the bottom to surround the location of the leak. The skirt supports a cover. A portion of the skirt or cover is made of an ionic and electrically permeable membrane to permit current flow. A second liquid is defined so as to be miscible with the first liquid and have a markedly different electrical conductivity. The rate of flow of the second liquid out of the lower skirt and cover is determined by measuring the electrical potential between the liquid in the impoundment and the second liquid within the skirt as the electrical conductivity of the surrounding earth is altered by invasion of the second liquid into the soil under the geomembrane liner. The apparatus utilizes a reservoir of the second liquid which is delivered through a suitable valve and fill hose into the lower skirt cover.

U.S. Pat. No. 4,905,210, issued on Feb. 27, 1990, to T. E. Owen describes a liquid impoundment survey vehicle that incorporates a position finding and tracking system. A set of hydrophones spaced around the impoundment detects a liquid transmitted acoustic pulse from the vessel. The vessel supports an RF transmitter which broadcasts a timing pulse. With the timing pulse elapsed acoustic travel time is measured to define range in the liquid. The range defines an arc of a circle around a single hydrophone.

U.S. Pat. No. 4,740,757, issued on Apr. 26, 1988, to Converse et al. describes a method and apparatus for locating leaks in a multiple layer geomembrane liner. In this apparatus, in the event of a tear or perforation formed in the lower liner, a current flow path is established from a power supply and conductors connected to the power supply. The current flow path extends through the liquid to the leak. Because of the liquid path through the liner, electrical current will flow through the perforation and establish an associated magnetic field in the near vicinity of the leak. Magnetic sensors are then swept across the surface of or through the impounded liquid above the liners to indicate such magnetic field variations and the locations of such perturbations corresponding to the location of the leak perforations.

U.S. Pat. No. 4,720,669, issued on Jan. 19, 1988, to T. E. Owen describes a geomembrane liner leak assessment shell shaped probe. This determines the size of a leak in a geomembrane liner by measuring the electric current density through the liner at locations suspected to contain a leaking penetration. By comparing the observed current flow through the liner, as measured by the assessment probe, with simulated current conducting contacts, the equivalent cross-sectional area of the leak perforation may be determined.

Finally, U.S. Pat. No. 4,543,525, issued on Sep. 24, 1985, to Boryta et al. shows a method for determining a leak in a pond liner of electrically insulating sheet material. This method immerses a power electrode in an electrically conductive fluid within the pond and a second or ground electrode in the supporting medium so as to create therewith an electrical potential between the pond fluid and the supporting medium. A detector, having a pair of spaced probe electrodes which are electrically connected, is introduced to the fluid near the power electrode with the ends of the probe electrodes adjacent the liner. The detector is rotated until a maximum current reading is obtained by a galvanometer electrically connected to the detector probes. With the probes so aligned with respect to the power electrode, the probes are caused to traverse the liner and the location of a leak is noted by a sharp change in the galvonometer reading as one of the probes passes over the leak.

It is an object of the present invention to provide a leak detector that is suitable for creating a position vector as to the leak location.

It is another object of the present invention to provide an impoundment leak detector that utilizes a sensor array for measuring electrical potentials.

It is a further object of the present invention to provide an impoundment leak detector that is suitable for detecting multiple leaks.

It is a further object of the present invention to provide an impoundment leak detector that is relatively easy to utilize, simple to manufacture, and relatively easy to install.

It is still a further object of the present invention to provide an impoundment leak detector that is non-intrusive.

These and other objects and advantages of the present invention will become apparent from a reading of the attached specification and appended claims.

SUMMARY OF THE INVENTION

The present invention is an apparatus and method for the detection of leaks in impoundment utilizing arrayed potentials. The apparatus of the present invention comprises a first electrode, a probe assembly having an injection electrode, and a power source electrically connected to the first electrode and to the injection electrode. The probe assembly has a plurality of sensor elements extending radially outwardly relative to the injection electrode. The sensor elements are suitable for sensing electrical potential at points distal to the injection electrode. A processor is interconnected to the sensor elements so as to determine a direction of current flow from the injection electrode.

In the present invention, the probe assembly further comprises a boom that extends upwardly from the injection electrode and a platform that is connected to the boom and is suitable for floating on the surface of a liquid. The platform is adjustable longitudinally along the boom so as to support the injection electrode a desired distance below the surface of the liquid. Each of the sensor elements extends radially outwardly from the boom. The sensor elements are positioned an equal distance from the injection electrode and from an adjacent sensor element. Specifically, four sensor elements are employed and each is separated by ninety degrees from an adjacent sensor element. The sensor elements are positioned on the end of an insulated rod. In addition, the sensor elements are positioned generally coplanar with the injection electrode.

The apparatus of the present invention is employed in an impoundment that includes a first containment layer and a second containment layer arranged therebeneath. The first and second containment layers define a space therebetween. The first containment layer and the space contain an electrically conductive solution, such as brine. The first electrode is positioned in this space. The probe assembly extends into the electrically conductive solution on the first containment layer.

The method of the present invention comprises the steps of: (1) positioning a first electrode in a brine-filled space between a first impoundment layer and a second impoundment layer; (2) positioning an injection electrode in a brine solution on the first impoundment layer: (3) arranging a plurality of sensor elements outwardly from the injection electrode so as to sense electrical potential distal to the injection electrode; (4) passing a voltage to the injection electrode such that this voltage passes to the electrically conductive brine solution; (5) measuring the electrical potential with the sensor elements; and (6) processing the electrical potential of each of the sensor elements so as to produce a positioned vector as to a location of a leak relative to the injection electrode.

This method further comprises the step of passing a current to the injection electrode such that the current flows from the injection electrode to the first electrode through the leak in the first impoundment layer. This method further includes the step of supporting the injection electrode and the sensing elements above the first impoundment layer in the brine solution.

For the detection of multiple leaks, the present invention employs the steps of: (1) repositioning the injection electrode and the sensing elements within the brine solution on the first impoundment layer; (2) passing a voltage to the repositioned injection electrode such that current flows through a leak toward the first electrode; (3) measuring the electrical potential of each of the sensor elements; and (4) processing the electrical potentials of the repositioned injection electrode and sensor elements so as to produce a derived vector of leak location. This derived vector of leak location is compared with the position vector of leak location so as to determine the existence of multiple leaks. These derived vectors are then iterrated so as to produce multiple vectors indicative of a position of such multiple leaks.

The present invention further describes a determination of leak location in the second impoundment layer through the measurement of transient induced potentials.

BRIEF DESCRIPTION OF THE DRAWINGS

FIG. 5A and 5B are diagrammatic sketches showing the technique for iterrating vectors so as to determine multiple leak locations.

DETAILED DESCRIPTION OF THE INVENTION

The present invention, as described herein, is suitable for the detection of leaks by two particular techniques. The first technique is the determining of leak location in the first impoundment layer by the measurement of arrayed potentials. This is to be considered the "preferred embodiment of the present invention" and is described, in particularity, in conjunction with FIG. 1-5. The alternative embodiment of the present invention shows the second technique for determination of leak location in the second impoundment layer. This technique is by the use of transient induced potentials. This alternative embodiment of the present invention is shown in conjunction with FIGS. 6-9. For the purposes of clarity, the preferred embodiment of the present invention, that is, the determination of leak location by the measurement of arrayed potentials, is described herein first.

Leak Location by Measurement of Arrayed Potentials

Figure 1:
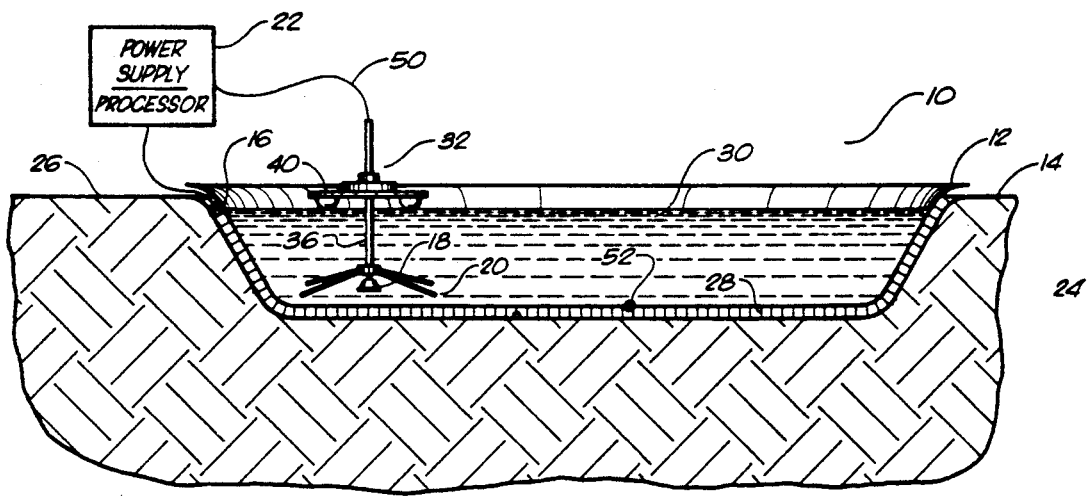
FIG. 1 is a cross-sectional view taken across the impoundment showing the preferred embodiment of the present invention.

Referring to FIG. 1, there is shown at 10, the leak detection system in accordance with the preferred embodiment of the present invention. Leak detection system 10 comprises a first impoundment layer 12, a second impoundment layer 14, a first electrode 16, an injection electrode 18, a plurality of sensor elements 20, and a power source 22. Each of these items cooperate so as to produce the leak detection system of the present invention.

As described herein previously, the first impoundment layer 12 is a polyethylene sheet. The second impoundment layer 14 is positioned beneath the first impoundment layer 12. The second impoundment layer 14 is also a polyethylene sheet. The polyethylene sheet of the second impoundment layer 14 generally lies in surface-to-surface contact with the earth 24. As can be seen, the first impoundment layer 12 and the second impoundment layer 14 are placed within an excavated area formed within the surface 26 of earth 24. This acts as an impoundment for the storage and disposal of chemicals and wastes. A polyethylene grid 28 is positioned between the first impoundment layer 12 and the second impoundment layer 14. The arrangement of the polyethylene grid 28 between the first impoundment layer 12 and the second impoundment layer 14 allows the leakage from the upper layer 12 to be directed to the sump by the bottom layer 14. In this way, leakage can be monitored, and when a predetermined leakage rate is reached, the impoundment is shut down for repairs to the liner (otherwise known as geomembranes). The present invention, in its preferred embodiment, is specifically designed for the location of leaks in the first impoundment layer 12.

It can be seen that a liquid 30 is received by the first impoundment layer 12. In normal use, this liquid 30 is a chemical or other waste or possibly brine or other industrial chemicals. However, when it becomes necessary to inspect for leaks, the liquid 30 should be an electrically between liquid, such as brine or water (which must be substituted for the waste). Additionally, the space 28 between the first impoundment layer 12 and the second impoundment layer 14 should also be filled with an electrically conductive liquid (such a brine) within the polyethylene grid.

For the purposes of detecting leaks, a probe assembly 32 is provided. Probe assembly 32 includes the injection electrode 18 and the sensor elements. As can be seen in greater detail in FIG. 2, the probe assembly 32 has the injection electrode 18 positioned at its lowermost end. The sensor elements are exposed metal electrodes 20, supported on the ends of insulated rods 34. The sensor elements 20 and the insulated rods 34 extend radially outwardly relative to the injection electrode 18. The sensor elements 20 are suitable for sensing electrical potentials and measuring such electrical potentials a locations distal to the injection electrode 18. The injection electrode 18 has a peculiar hemispherical configuration. The theory of the present invention is directed toward a mathematical derivation of the position vector from the injection electrode position to the leak position. The theory requires that the current be modelled as emanating from a point interior to the injection electrode, which constraints the injection electrode to a sphere, ideally. The hemispherical embodiment is required because the probe is normally placed at the bottom of the impoundment. Since the boundary mirrors the system, a hemispherical shape is required to mirror into a sphere. Also, it established a more uniform flat surface so as to more easily place the sensor elements 20 in coplanar relationship with the injection electrode 18.

The probe assembly 32 includes a boom 36 that extends upwardly from the injection electrode 18. As can be seen, the insulated rods 34, and their associated sensor elements 20, extend radially outwardly from collar 38 around the boom 36. It can be seen that the insulated rods 34 extends radially and diagonally downwardly from the collar 38 so as to be placed in coplanar alignment with the injection electrode 18. A platform 40 is connected around the boom 36. Platform 40 has a generally flat surface 42. Suitable floats 44 are provided on the under side 46 of platform 40 so as to allow the platform 40, and the associated structure of the probe assembly 32 to suitably float on the surface of a liquid. The platform 40 is adjustable longitudinally along the boom 36. As such, the distance between the platform 40 and the injection electrode 18 can be varied as needed. This allows the injection electrode to be placed a desired distance below the surface of the liquid 30 or above the first impoundment layer 12. The present invention, thusly, allows the probe assembly 32 to be adapted, as needed, within the confines of the impoundment.

Referring back to FIG. 1, a multi-conductor cable 50 is connected to the probe assembly 32. Cable 50 allows for the transmission of multiple signals from each of the sensor elements 20. The cable 50 also allows for the passing of a current to the injection electrode 18 at the bottom of the probe assembly 32.

The first electrode 16 also extends from the power supply/processor 22. The first electrode 16 is positioned within the space between the first impoundment layer 12 and the second impoundment layer 14. As stated previously, the space containing the grid 28 is suitably filled with an electrically conductive solution, such as brine. This brine can be introduced into the space by way of any leak within the first impoundment layer 12 or can be directly injected into this area. It is only important to the functioning of the present invention that an electrically conductive liquid be provided in both the area above the first impoundment layer 12 and above the second impoundment layer 14. By positioning the first electrode 16 in the position illustrated in FIG. 1, the first electrode 16 can suitably receive any current that would pass from the injection electrode 18, through the brine solution 30, through the leak 52 and through the brine solution within the space containing the grid 28.

Figure 2:
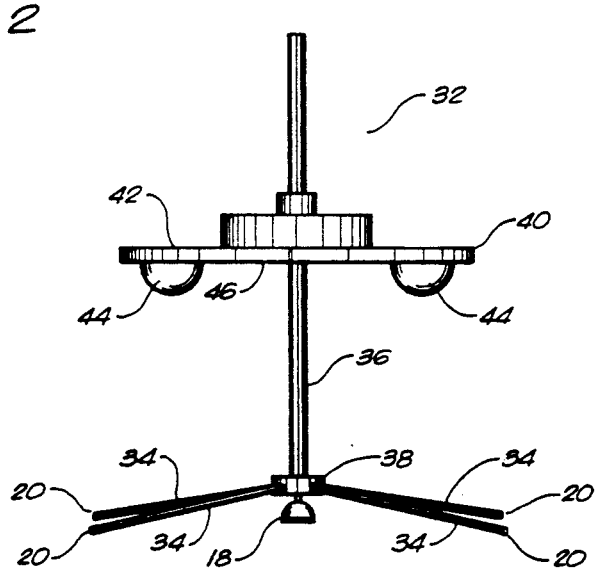
FIG. 2 is a view, in side elevation, of the probe assembly in accordance with the preferred embodiment of the present invention.

With reference to FIGS. 1 and 2, the present invention superficially resembles the existing practice of injecting an electric current into a liquid-filled impoundment via an immersed electrode. The circuit is completed via another electrode placed between the two geomembrane layers. A voltage is applied across the electrodes. In this manner, it is possible for current to flow through the upper membrane leak discontinuities. The impoundment is then surveyed with electric dipole potential measurements (voltage measurements between pairs of points in the liquid). As an example, see U.S. Pat. No. 4,543,525 of Boryta et al. At present, there are techniques used for mapping current densities in the impoundment which reveal probable leaks, on the basis of these dipole measurements.

However, the present invention is different from the present state of the art in that the current injection point 18 is near the measurement point. In fact, the functions of injection and measurement are combined into the single probe assembly 32 which consists of the floating platform 40, plus the probe array suspended by the movable four to five meter long boom 36. The platform 40 may include suitable components such as a servo for raising and lowering the probe array along the boom 36 and an electronic assembly containing suitable instrumentation amplifiers, data conversion and transmission components, servo controls, and the like. The major departure of the present invention from the prior art is in its ability to establish a position vector from the probe assembly 32 to the nearest leak. The vector is derived from the potentials measured by the probe array elements. The probe array is shown in greater detail in conjunction with FIG. 3.

Figure 3:
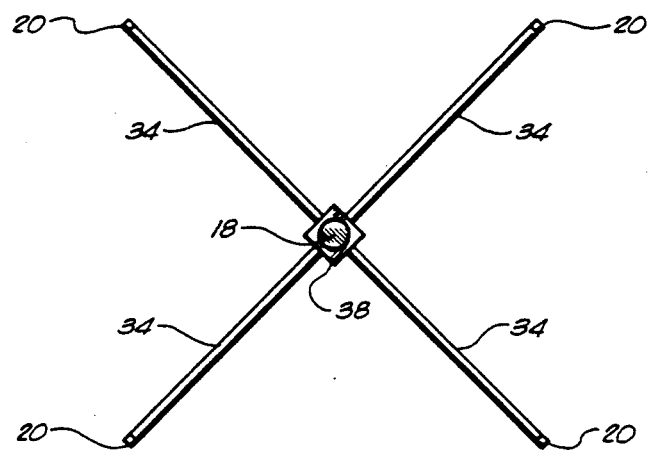
FIG. 3 is a bottom view of the probe assembly in accordance with the preferred embodiment of the present invention.

In FIG. 3, it can be seen that the injection electrode 18 is positioned centrally of the insulated rods 34 and the sensor elements. It can be seen from FIG. 2 that the injection electrode 18 has a hemispherical shape. The collar 38 extends above the injection electrode 18 and has a rather square configuration. Each of the insulated rods 34 extends outwardly from the collar 38 at right angles (ninety degrees) to each adjacent insulated rod. Each of the sensor element electrodes 20 is positioned an identical distance from the injection electrode 18. Each of the sensor element electrodes 20 are also separated from adjacent sensor element electrodes 20 by an equal distance. As such, the probe assembly 32 takes on a rather symmetrical configuration. A total of four sensor elements are provided in the probe assembly of the present invention.

Figure 4:
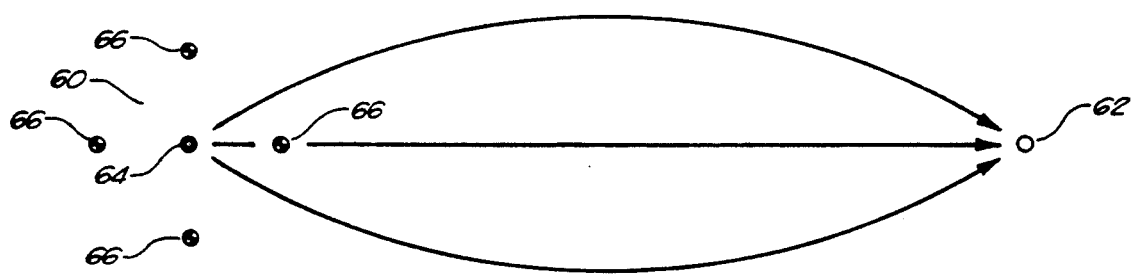
FIG. 4 is a diagrammatic view of the method of processing sensed information so as to indicate leak location.

FIG. 4 shows a schematic representation of the probe array 60 and the location of a leak 62 near the array 60. The probe array 60 includes the injection electrode 64 and the sensor elements 66. The leak and the sensor elements 66 are assumed to be in the same plane. This assumption is borne out in practice since the probe array is positioned by the servo to the bottom of the impoundments. Current flows between the leak 62 and the injection electrode 64. As such, there is an electric potential at any point in the fluid, as measured with respect to the injection electrode 64. The sensors 66 measure the potentials at four points with respect to the injection electrode 64, and these values are digitized for use in computation algorithms.

For a known leak location and a known current between the injection electrode 64 and the leak the potential at any point can be calculated directly. It can be shown that for a given applied voltage a leak at any location will generate a unique set of probe potentials, i.e. potentials measured at each probe element with respect to the injection electrode, and by extension, this set can be determined from the known leak location by direct calculation. Furthermore, the reverse is true for leaks of unknown location. A leak of unknown location can be located by using the probe potentials generated. By measuring the probe potentials as received by the sensors 66, a position vector can be derived so as to locate the leak 62 relative to the location of the probe.

With reference to FIGS. 1-4, the method of the present invention is described as follows. Initially, the first electrode 16 is positioned in the brine-filled space containing the grid 28 between the first impoundment layer and the second impoundment layer 14. The probe assembly 32, with its injection electrode, has been introduced into the conductive fluid 30 on the first impoundment layer 12. The probe assembly 32 includes the array of sensor elements arranged outwardly from the injection electrode 18. The power supply 22 then passes a voltage to the injection electrode 18, inducing current to flow, the magnitude of which is dependent upon fluid conductivity, leak size, leak distance from probe, applied voltage, and size of injection electrode. The electrical potential is then measured with the sensors 20 a given distance from the injection electrode 18. The electrical potential of each of the sensor elements is then processed so as to produce a position vector as to the location of the leak 52 relative to the injection electrode 18.

In normal operation, the current from the injection electrode 18 will pass into the electrically conductive solution 30 so as to pass through the leak 52, into the brine solution contained within the space containing the grid 28 and to the first electrode 16 so as to complete the electrical circuit. If there is no leak, then the only current to flow would be leakage current across the membrane. When a leak is present, the processor 22 goes into action so as to determine the position vector of the leak with respect to the location of the probe assembly 32 within the impoundment.

The Environmental Protection Agency at present has regulatory jurisdiction over impoundment operation, and among the proposed rules, there would be maximum allowances for leakage rates. These rates are routinely monitored as sump pumping volumes. Impoundment shutdown would be required when the leakage rate per square meter of geomembrane exceeds the mandated threshold. There exists data that relates the size and spatial distribution of geomembrane leaks located after shutdown to the leakage rates measured prior to shutdown. This data is incorporated into the algorithms used by the processor 22 of the present invention.

In conducting an impoundment survey, the procedure involves a series of manual operations directed by software. This is the actual measurement process. The software would have access to the impoundment statistics using engineering data and the most recent leakage rate data. The operators would be directed to the measurement locations determined by software, and it would be the operator's responsibility to place the probe assembly to these locations in the impoundment, which has been drained and partially filled with mild brine or other conductive fluid. The space between the membranes should be filled with strong brine to assure that all leaks are at the same potential. This is required for the accurate location of multiple leaks. There would need to be at least as many measurement locations as leaks and the reason for this will become apparent. Actually, there would probably need to be many more measurements than leaks in order to obtain reliable performance.

With reference to FIG. 5A and 5B, the multiple leak problem is determined in a peculiar way. In FIG. 5A and 5B, it can be seen that there are leaks 70 and 72. The probe assembly is shown as utilized in two measurement positions 74 and 76. The initial computational result would be two derived vectors pointing to two points between the two leaks, due to error. The points would lie on an arc connecting the two leaks. If at least one of the measurement positions is non-equidistant from the two leaks, then it is possible to perform iterative recalculation of the derived vectors with the recalculation of each using the last calculation of both. In FIGS. 5A and 5B, the process is diagrammed showing initial derived vectors as solid. Successive calculations derive vectors (shown dashed) that are approaching the leaks. Each recalculation of the derived vectors would yield a better estimate of the actual leak position vectors. If one measurement position is equidistant from the leaks, its vector would approach the leak not approached by the other vector. So N number of measurements are required to find N leaks. After completion of the aforestated procedure, the operation could continue with the option of a search mode, allowing movement of the probe to exact leak locations, thereby refining the survey.

The use of the probe assembly and processor of the present invention, and the mathematics associated with the determination of the proper vector provides the user of the present system with the ability to determine leak location and size in the upper geomembrane of the impoundments. As such, the present invention uses the measurement of arrayed potentials. The use of the vector analysis allows for a relatively easy calculation and determination of the exact location of the leak within the system. As a result, t he present invention achieves advantages not found in prior art systems by using a non-intrusive technique for the determination of leak sizes and locations in the upper impoundment layer.

Leak Location by Measurement of Transient Induced Potentials

An alternative embodiment of the present invention is related to the determination of leaks in the lower liner of the impoundment. The technique of measurement of transient induced potentials is related to the existing practice of injecting current into a medium in the impoundments and making measurements of the patterns of current flow to determine likely leak locations. However, the present invention is particularly used for the location of leaks in the bottom layer of the geomembranes.

As to be expected, there are more difficulties to overcome in divising and operating a system to perform the present task in comparison to the leak location for the upper liner and the technique of arrayed potentials, described herein previously. Since there is no way to have the injection point movable in the space between the layers, it is necessary to allow for the possibility of having a single injection point or otherwise a severely constrained set of points for the injection.

Figure 6:
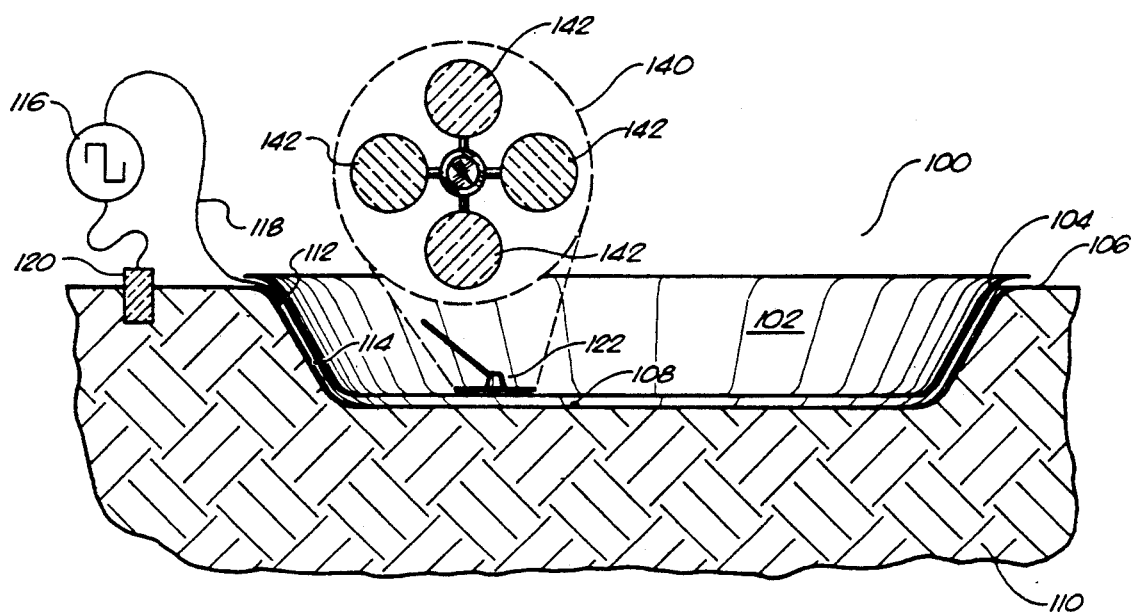
FIG. 6 is a schematical representation showing the use of transient induced potentials for determining leaks in the second impoundment layer.

The system for the measurement of the transient induced potentials for the determination of leak location in the bottom layer is shown as system 100 of FIG. 6. In the representation of FIG. 6, it can be seen that the impoundment 102 has a first impoundment layer 104 and a second impoundment layer 106. The second impoundment layer 106 includes a leak 108. The second impoundment layer 106 is arranged in close proximity to the excavated earth 110. A first electrode 112 is placed in the space 114 between the upper impoundment layer 104 and the lower impoundment layer 106. The first electrode 112 is placed in a conductive brine solution in the space 114. A generator 116 is connected by line 118 to this electrode. The generator 116 is also connected to a grounded electrode 120. The generator 116 outputs a square wave driving voltage.

The basis of operation of the present invention requires a square wave because this is basically an AC-based measurement system requiring a high frequency bearing signal. It must also have a fundamental period long enough to make possible synchronous detection. The long period is required because the wave length needs to be long in comparison to the dimensions involved. These dimensions are the distances between the electrodes 112 and 120, and the leak 108. A detector instrument 122 is provided so as to carry out measurements associated with the system of the present invention.

Figure 7:
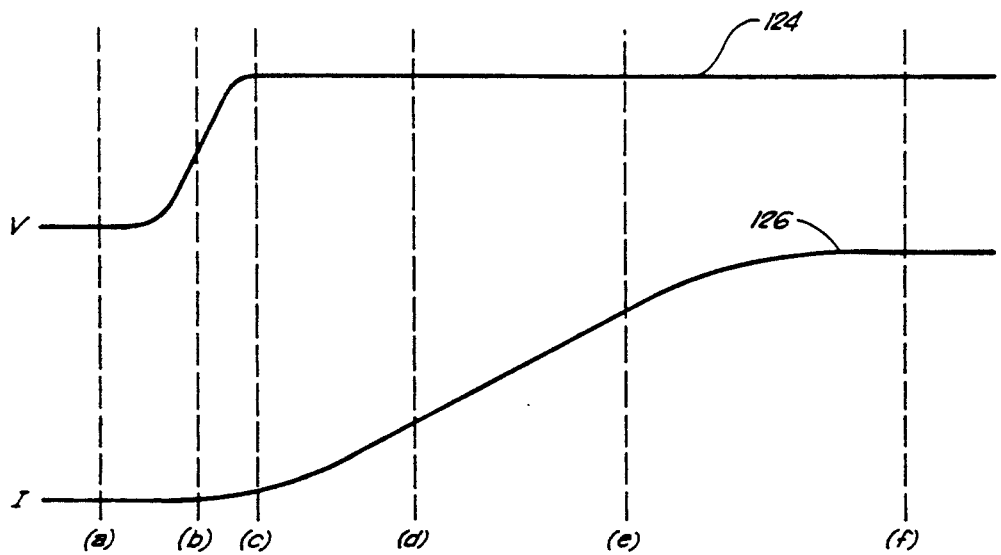
FIG. 7 is a graphic illustration of voltage and current during the leak detection scheme of FIG. 6.

Referring to FIG. 7, the wave shapes produced by the generator 116 in conjunction with the electrodes 112 and 120 and the leak 108 is provided. The top wave shape 124 is the rising edge of the driving voltage. The bottom wave shape 126 is the resulting current profile in a typical time relationship. The voltage rise time is as short as practical. The current rise time is lagging because of charge carrier (ion) inertia in the impoundment fluid. This is an order of magnitude higher than in free electron flow. This inertial component in the inter-layer space would also be much higher than that of the ions in the earth conductor (because they are much more confined) with the result being much higher mean velocity.

Figure 8A:
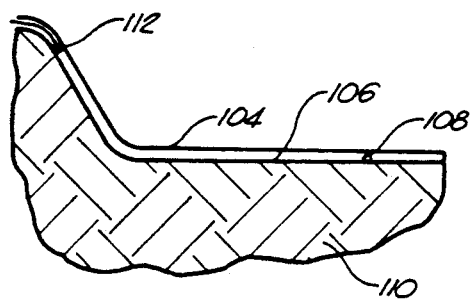
FIG. 8a-f the timed electrical pulse affecting the system of leak locations shown in FIG. 6.
Figure 8B:
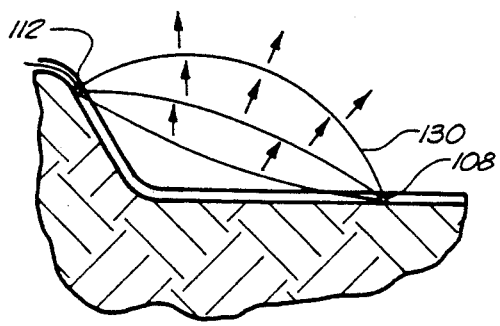
Figure 8C:
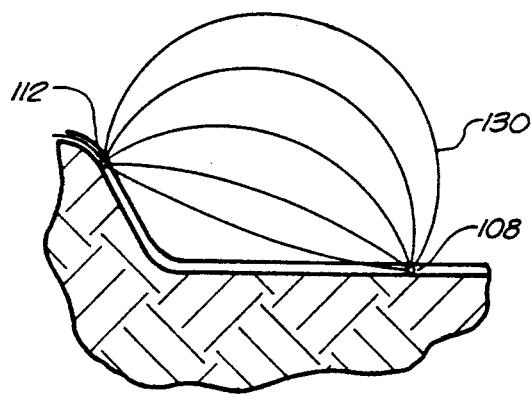
Figure 8D:
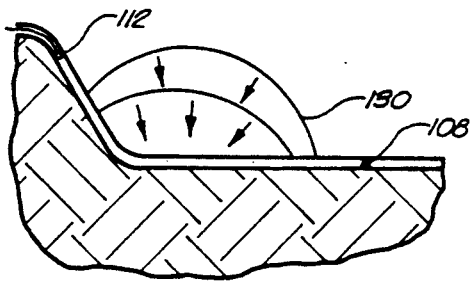
Figure 8E:
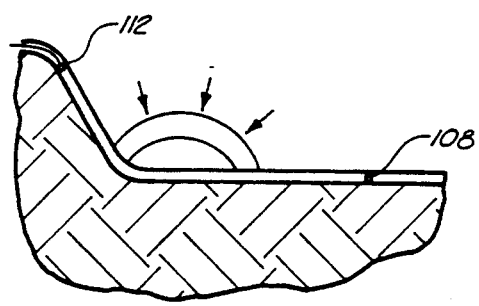
Figure 8F:
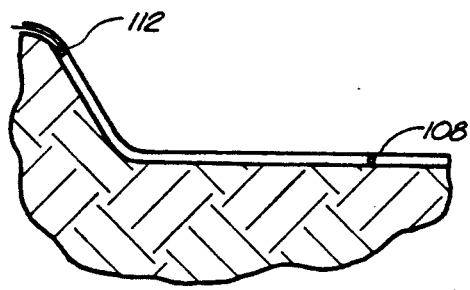

The time markers superimposed in FIG. 7 are for relating the current and voltage profiles to the events shown in FIGS. 8a-f. FIG. 8(a) shows the system at the beginning of signal production. For simplicity purposes, it is necessary to assume that the voltage at the leak 108 closely tracks the potential at the earth connection 120 to the generator 116 (or that the earth is an ideal conductor). In FIG. 8(b), the current is lagging the voltage, as such, the electrical field lines 130 in FIG. 8(b) are shown as expanding across the area between the first electrode 112 and the leak 108. In FIG. 8(c), the driving voltage is no longer increasing at a rate so as to create an expanding field. In FIG. 8(c), it can be seen that the field 130 is shown as a static, non-expanding field, between the first electrode 112 and the leak 108. In view of the use of the square wave driving voltage of the generator, as might be expected, FIG. 8(d) depicts the resulting collapse of the field 130 as current continues to increase while voltage remains constant. FIG. 8(e) shows the continued collapse of the field toward a central point between the first electrode 112 and the leak 108. A strictly mechanical description of this phase includes the fact that as charge carriers attempt to migrate along the field lines, they encounter the boundaries of the conductor (the liner surfaces) as they pile up along these barriers. The accumulating charge begins to deflect the field external to the boundaries. This continues until FIG. 8(f) in which the field lines have all been deflected inwardly so that all of the field is channeled between the two layers. As a result, no external field is shown.

The above-described sequence suggests that the alternating buildup of charge on the inner surface of the upper layer 104 could be detected with capacitance plates. A possible arrangement of these capacitance plates is shown in the inset 140 of FIG. 6. As can be seen, the detector 122 includes two opposing pairs of capacitance plates 142. Each pair of capacitance plates 142 represents orthogonal components of a direction vector. The inner surface charge of redistribution occurs in waved fashion starting at the submerged electrode 112 and at the leak 108. The two waves meet at midpoint between the starting points, depending somewhat on the mass difference of the positive and negative ions. As this polarization wave passes by the capacitance plates 142, it generates a pulse across the pairs of plates. The two pairs of plates give pulse amplitudes related to their respective orientation to the polarization wave front.

Figure 9:
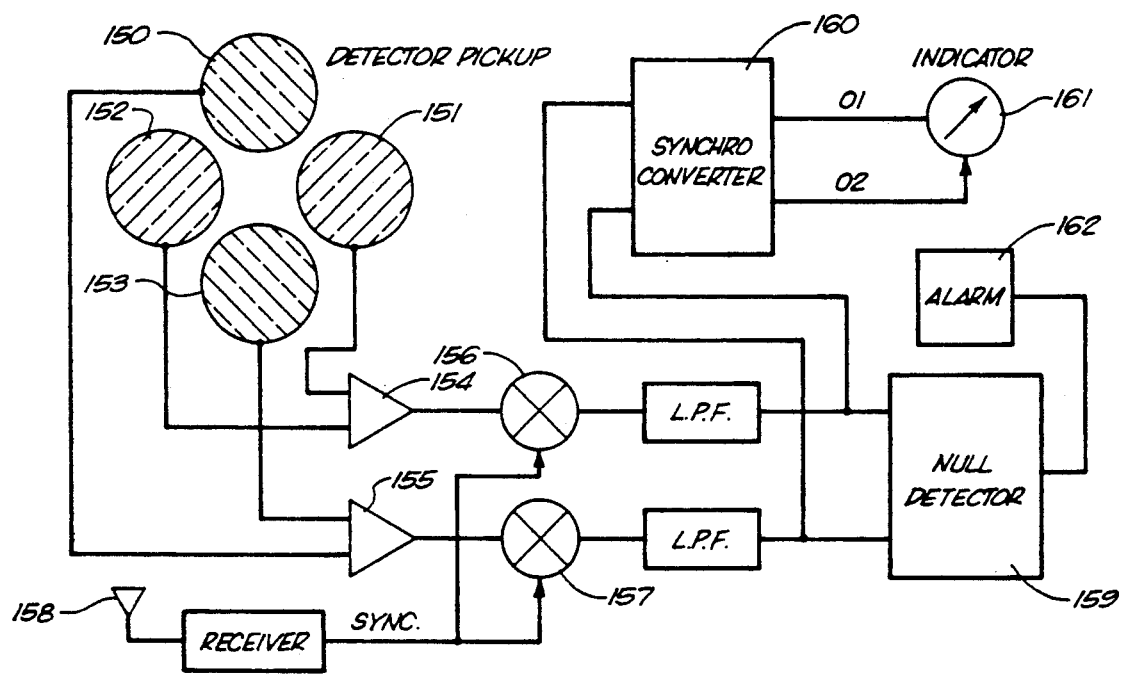
FIG. 9 is a schematical representation of the system of leak location by the measurement of transient induced potentials.

FIG. 9 shows a schematic diagram of a possible system for performing a leak search on the lower layer 106 of the geomembrane liner. In the top left are the capacitive pick-up plates 150, 151, 152, and 153. Each of the capacitive pick-up plates 150, 151, 152, and 153 are shown connected, in pairs, to instrumentation amplifiers 154 and 155. The plates generally need to be encapsulated for electrical protection of the amplifiers. After amplification, the signals are directed to a pair of synchronous switches 156 and 157 so that the pulse amplitude and polarity can be converted to DC voltage. The synchronizing signal may be transmitted by radio 158 from the square wave generator to the detector 159. The two DC voltages are applied to a synchro converter 160 for driving an indicator 161.

In use, the instrument would be operated in a search mode. The operator would observe the indicator 161 which would point perpendicular to the polarization wave front. By moving the detector in the direction pointed to by the indicator 161, the operator would eventually encounter the leak. When the detector is centered over the leak, the DC output of the synchronous switches would null. This would be detected by the null detector 159 so as to activate the alarm 162. As such, the leak in the lower layer could be properly determined.

The foregoing disclosure and description of the invention is illustrative and explanatory thereof. Various changes in the details of the illustrated apparatus, or in the details of the method of the present invention, may be made within the scope of the appended claims without departing from the true spirit of the invention. The present invention should only be limited by the following claims and their legal equivalents.

I claim:

1. An apparatus for the detection of leaks in an impoundment having at least one containment layer comprising:

a first electrode adapted to be positioned adjacent one side of the containment layer;

a probe assembly having an injection electrode connected thereto, said probe assembly having a plurality of sensor elements extending radially outwardly relative to said injection electrode, said sensor elements for sensing electrical potentials at points distal to said injection electrode, said injection electrode having a hemispherical configuration, said injection electrode adapted to be positioned such that a flat surface of said hemispherical configuration is adjacent another side of the containment layer;

a power source electrically connected to said first electrode and to said injection electrode, said power source for producing a current in said injection electrode, said current passing between said injection electrode and said first electrode through any leak in the containment layer; and processor means interconnected to said sensor elements, said processor means for determining a direction of current flow from said injection electrode as sensed by said sensor elements.

2. The apparatus of claim 1, said probe assembly further comprising:

a boom extending upwardly from said injection electrode; and a platform means connected to said boom, said platform means for floating on a surface of a liquid.

3. The apparatus of claim 2, said platform means adjustable longitudinally along said boom, said platform means for supporting said injection electrode a desired distance below the surface of the liquid.

4. The apparatus of claim 3, said plurality of sensor elements comprising:
   four sensor elements extending radially outwardly from said boom, each of said sensor elements positioned an equal distance from said injection electrode, each of said elements separated by ninety degrees from an adjacent sensor element.

5. The apparatus of claim 4, each of said sensor elements positioned on an end of an insulated rod.

6. The apparatus of claim 1, said sensor elements positioned generally coplanar with said injection electrode.

7. The apparatus of claim 1, said impoundment comprising:
   a first containment layer; and
   a second containment layer arranged beneath said first containment layer, said first and second containment layers defining a space therebetween said first containment layer and said space containing an electrically conductive solution, said first electrode positioned in said space, said probe assembly extending into said electrically conductive solution on said first containment layer.

8. A system for leak detection in an impoundment comprising:
   a first impoundment layer containing a brine solution;
   a second impoundment layer positioned beneath said first impoundment layer, said first and second impoundment layers defining a brine-filled space therebetween;
   a first electrode positioned in said brine-filled space;
   an injection electrode positioned in said brine solution on said first impoundment layer;
   a plurality of sensor elements extending outwardly from said injection electrode, said sensor elements for sensing electrical potentials at points distal to said injection electrode;
   a power source electrically connected to said first electrode and said injection electrode, said power source for passing a current to said injection electrode, said current passing between said injection electrode and said first electrode through a leak in said first impoundment layer; and
   a probe assembly connected to and supporting said injection electrode and said plurality of sensor elements in said brine solution, said probe assembly comprising:
   a boom extending upwardly from said injection electrode, said sensor elements extending outwardly from said boom adjacent said injection electrode; and
   a platform connected to said boom, said platform floating on said brine solution.

9. The system of claim 8 said platform adjustably connected to said boom for controlling a position of said injection electrode relative to a surface of said brine solution.

10. The system of claim 8, said sensor elements arranged generally coplanar to said injection electrode, each of said sensor elements separated by an equal distance from an adjacent sensor element.

11. The system of claim 10, said plurality of sensor elements comprising four sensor elements positioned on insulated rods extending outwardly from said injection electrode, each of said insulated rods separated by ninety degrees from an adjacent insulated rod.

12. The system of claim 8, further comprising:
   processor means interconnected to said sensor elements, said processor means for determining a direction of current flow from said injection electrode as sensed by said sensor elements.

13. A method of detecting and locating leaks in an impoundment comprising the steps of:
   positioning a first electrode in a brine-filled space between a first impoundment layer and a second impoundment layer;
   positioning an injection electrode in a brine solution on said first impoundment layer;
   arranging a plurality of sensor elements outwardly from said injection electrode, said sensor elements for sensing electrical potential;
   passing a voltage to said injection electrode such that a current passes through a leak in said first impoundment to said first electrode;
   measuring the electrical potential with said sensor elements a distance from said injection electrode;
   processing the electrical potential of each of said sensor elements so as to produce a position vector as to a location of the leak relative to said injection electrode;
   repositioning said injection electrode and said sensing elements within said brine solution on said first impoundment layer;
   passing a voltage to the repositioned injection electrode such that current flows through a leak toward said first electrode;
   measuring the electrical potential of each of said sensor elements; and
   processing the electrical potentials of the repositioned injection electrode and sensor elements so as to produce a derived vector of leak location;
   comparing the derived vector of leak location of the repositioned injection electrode with the position vector of leak location so as to determine the existence of multiple leaks; and
   iterrating the derived vectors so as to produce multiple vectors indicative of a position of such multiple leaks.

14. The method of claim 13, further comprising:
   passing a current to said injection electrode such that current flows from said injection electrode to said first electrode through the leak in said first impoundment layer.

15. The method of claim 13, further comprising:
   supporting said injection electrode and said sensing elements above said first impoundment layer in said brine solution.

* * * * *